United States Patent [19]

Elsley et al.

[11] 4,307,612
[45] Dec. 29, 1981

[54] METHOD AND MEANS FOR ULTRASONIC INSPECTION

[75] Inventors: Richard K. Elsley; R. Bruce Thompson, both of Thousand Oaks, Calif.

[73] Assignee: Electric Power Research Institute, Inc., Palo Alto, Calif.

[21] Appl. No.: 86,511

[22] Filed: Oct. 19, 1979

[51] Int. Cl.³ ............................................. G01N 29/04
[52] U.S. Cl. ........................................ 73/613; 73/620
[58] Field of Search .................. 73/602, 613, 620, 624

[56] References Cited

U.S. PATENT DOCUMENTS 3,295,362 1/1967 Wood et al. .......................... 73/613
4,213,184 7/1980 Fasching .......................... 73/613 X

OTHER PUBLICATIONS

"Donar: A Computer Processing System to Extend Ultrasonic Pulse Echo Testing", by Lees et al., from Ultrasonics, Jul. 1973.

Primary Examiner—James J. Gill
Attorney, Agent, or Firm—Flehr, Hohbach, Test

[57] ABSTRACT

Ultrasonic inspection of a structure such as steel tubing is enhanced by moving the ultrasonic wave transmitter and receiver through the pipe and periodically injecting an ultrasonic pulse into the tube. Reflected waves are received during a sample period after each pulse injection. By proper selection of linear displacement between pulses and the sample time interval, the time reference of received signals can be adjusted whereby signals reflected from only one direction are coherently added.

6 Claims, 2 Drawing Figures

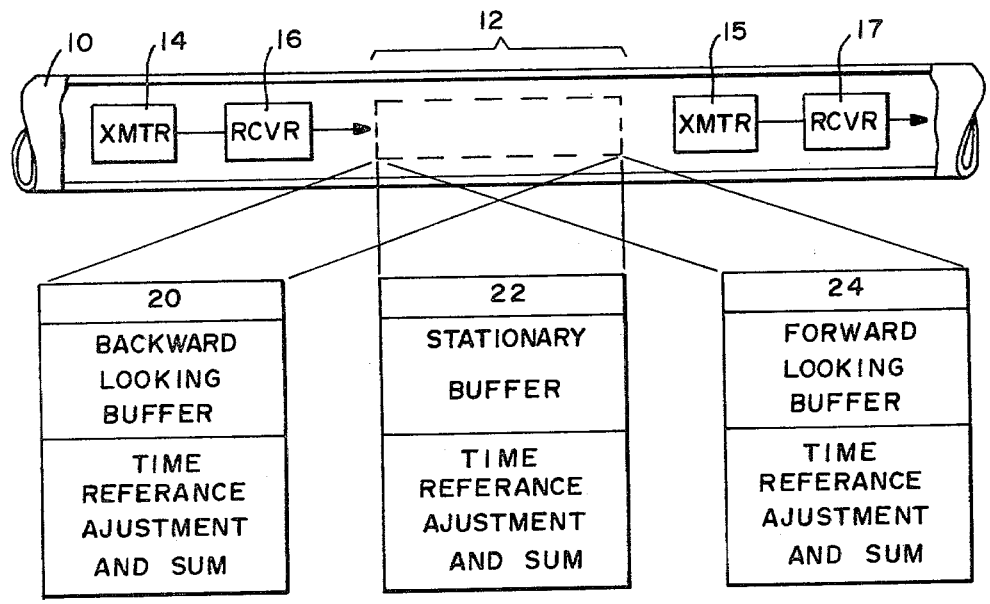
FIG.—1
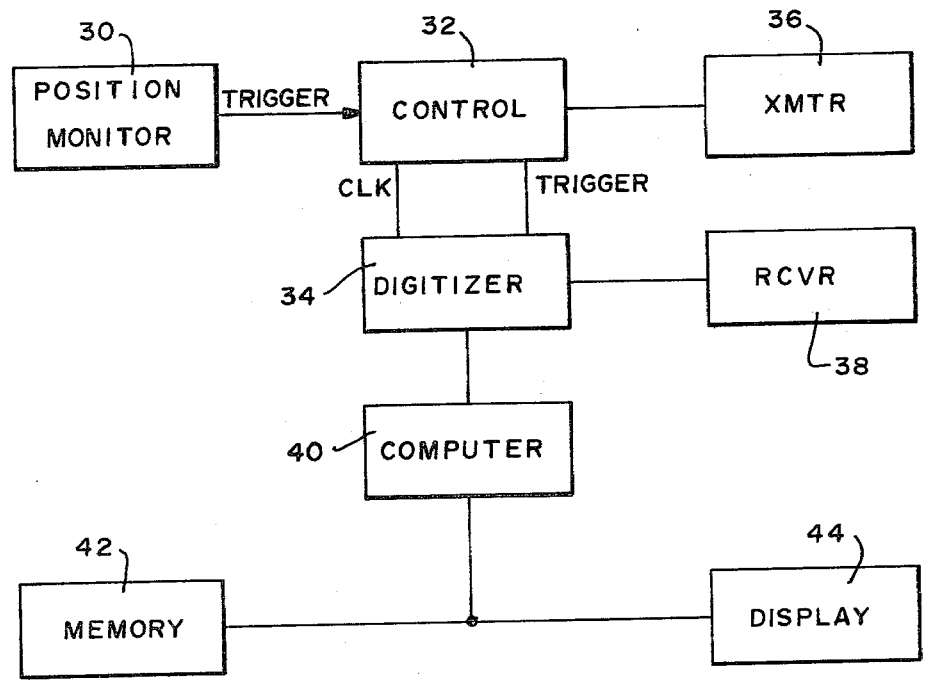
FIG.—2

METHOD AND MEANS FOR ULTRASONIC INSPECTION

This invention relates generally to non-destructive inspection of structures for defects, and more particularly the invention relates to a method and apparatus for ultrasonic inspection.

The inspection of steam and water transmission tubes in boiling and pressurized water power generation equipment is essential to ensure safe and dependable operation of such power systems. A number of non-destructive techniques are known for inspection of transmission tubes for such flaws as cracks, dents, and pits which could cause structural failure under prolonged operating loads.

In ultrasonic test systems, a wave is introduced into the inspected structure and the waves reflected from or attenuated by structural flaws are detected. Through analysis of these waves the size and location of defects can be determined.

The accuracy and dependability of ultrasonic inspection systems depends upon the sensitivity thereof to reflected ultrasonic waves. Heretofore, many defects which can be detected under optimum conditions can go undetected due to noise in the received signals.

Accordingly, an object of the present invention is improved method and apparatus for ultrasonically inspecting a body for defects.

Another object of the invention is a method of transmitting, receiving, and processing ultrasonic waves to improve the signal to noise ratio thereof.

Still another object of the invention is apparatus for processing signals whereby information content is improved and noise content is diminished.

Yet another object of the invention is a method of detecting and analyzing unidirectional ultrasonic signals.

Briefly, in accordance with the present invention, ultrasonic waves are introduced into a structure by transducer means as the transducer means is moved relative to the structure.

Ultrasonic waves are received by the transducer means for an interval of time after each introduction of an ultrasonic wave, and the time reference of the received waves is adjusted to compensate for displacement of the transducer means. The adjusted waves are then summed whereby the signal to noise ratio of the composite signals is improved.

More particularly, signals from waves reflected from defects in the structure lying in the direction of movement of the transducer means are enchanced by decreasing the delay in the time reference of the received waves by a time interval equal to twice the displacement of the transducer means between introductions of waves to the body divided by the velocity of the ultrasonic wave. In addition, waves received from defects in the body lying in a direction from which the transducer means is moved are enhanced by increasing the delay of the time reference of the received waves by a time equal to twice the displacement of the transducer means between introductions of waves into the body divided by the velocity of the ultrasonic wave. If separate transducer means are employed for introducing and receiving the ultrasonic waves, and waves reflected from defects are desired to be detected, the same procedures are used. If wave propagating directly from the transmitting means to the receiving means are to be detected, however, the signals are summed without an adjustment in time reference.

Where digital signal processing is utilized, it is advantageous to select the displacement of the transducer means between wave pulses to be a multiple of the speed of the ultrasonic wave multiplied by one-half of the sample time interval of received wave. This will ensure that equivalent points on each waveform will be digitized on successive repetitions of the measurement, so that the additions are coherent.

Further, cancellation of unwanted signals is increased by selecting the displacement of the transducer means between periodic signal introductions to be an odd multiple of one-eighth the wavelength of the ultrasonic signal.

While the method and apparatus can be embodied to use either analog or digital signal processing, in a preferred embodiment the received signals are digitized to facilitate the precision and flexibility of processing.

The invention and objects and features thereof will be more readily apparent from the following detailed description and appended claims when taken with the drawing, in which:

FIG. 1 is a functional block diagram illustrating one embodiment of the method of ultrasonic inspection in accordance with the present invention.

FIG. 2 is a functional block diagram of one embodiment of apparatus for ultrasonic inspection in accordance with the present invention.

Referring now to the drawings, FIG. 1 is a functional block diagram illustrating a portion of a body such as a tube 10 shown partially in section view with a segment 12 thereof being inspected for defects. In inspecting the tube 10 an ultrasonic transmitter 14 introduces an ultrasonic wave in the body of tube 10 and an ultrasonic receiver 16 receives ultrasonic waves in the tube during an interval of time after the introduction of an ultrasonic pulse by the transmitter 14. Thus, by appropriate timing of the receiver 16 reflected waves from defects in the segment 12 will be received by the receiver.

In order to inspect the length of the tube, the transmitter and receiver are pulled through the tube, and receiver 16 may receive reflected waves from defects in tube 10 which lie ahead of receiver 16. Conversely, when the transmitter and receiver are at positions 15 and 17, respectively, reflected waves from the defects in segment 12 are received from a direction opposite to the travel of the transmitter and receiver. Accordingly, it will be appreciated that in periodically introducing signals and in collecting the received signals for coherent addition, consideration must be given to the speed of travel of the transmitter and receiver and the direction from which the reflected waves are received.

Assuming that the transmitter 14 and receiver 16 were stationary, transmitter 14 could be pulsed and reflected waves could be received by receiver 16 and recorded. Since the transmitter and receiver are not moving the received waves could be directly added using the triggering of the transmitter as a common reference for the received waves. Assuming that all sources of noise within the tube 10 are random, coherent addition of the signals will reinforce the reflected signals and minimize the noise content thereby improving the signal to noise ratio of the summed signals.

However, in inspecting a tube it is desirable to move the transmitter and receiver linearly through the tube so that the entire length of the tube is inspected.

By judicious selection of the linear displacement of the transmitter between signals and the sample time interval, the time reference of received signals can be adjusted whereby only signals reflected from the direction of movement of the receiver are coherently added. Alternatively, the time reference can be adjusted whereby only the signals reflected in the direction from which the transmitter and receiver have moved are coherently added. Still further, the received signals can be added without time adjustment whereby only signals transmitted in one direction and received from the other direction are coherently added.

Assume that between transmitted pulses the transmitter and receiver combination move a distance, $\Delta x$. Signals from flaws ahead of the transducers will arrive earlier by time $T = 2\Delta x/C$ and signals arriving from behind the transmitter and receiver will arrive later by a time $T = 2\Delta x/C$, where C is the velocity of the ultrasonic wave. Signals which are transmitted in one direction and received from the other direction will have a fixed time reference.

By adding each received signal in three different buffers 20, 22, and 24, with a time reference displacement which compensates for the late, stationary, or early arrival of the waves, three composite waves can be obtained through summing the time reference adjusted signals wherein only the desired signals are added and all other signals and noise are substantially reduced by the addition process.

In order for the addition of the signals to be coherent, the displacement $\Delta x$ of the transmitter between signal transmissions must be a multiple of the ultrasonic wave speed times one-half the sample interval time period or $$\Delta x = MC\Delta t/2$$

Further, for more efficient cancellation of the unwanted signals, the displacement $\Delta x$ is preferably selected to be an odd multiple of one-eighth the wavelength of the ultrasonic signal applied to the tube, or $$\Delta x = N\lambda/8$$

FIG. 2 is a functional block diagram of apparatus for carrying out the ultrasonic inspection in accordance with the present invention. The position monitor 30 may be a conventional rotary transducer comprising part of the receiver or transmitter probe and which converts motion of the probe into a series of digital pulses (e.g. 1,000 pulses per revolution of shaft). The pulses are used to time the firing of the transmitter and provide a reference point in the digital processing of received signals.

In one embodiment the control box 32 contains counting circuitry which converts this sequence of pulses into a trigger signal every 0.134 inch of probe motion. In addition, the control box generates a tone burst of 342 KHz center frequency which is applied to the transmitter 36 and a 912 KHz clock which is applied to the digitizer circuitry 34. These values satisfy the previous equations when one selects M=2, N=3, and C=0.122 in/$\mu$sec. The transmitter and receiver can be an electromagnetic transducer of the type disclosed in U.S. Pat. No. 4,127,035 or of the type disclosed in copending application Ser. No. 086,512, filed Oct. 19, 1979. The digitizer is conventional and may be a Biomation 8100 Transient Recorder.

By digitizing the received signal, a computer 40 can be programmed to manipulate the signals for additive storage in memory 42. In addition, a display 44 can be provided for display of the stored signals. Memory 42 may be a floppy disc, display 44 may be a Tetronix 4006 display terminal, and the computer can be a microcomputer such as a Micronova.

In the described embodiment the transmitter and receiver were pulled through an Inconel tube at a rate of 12 inches per second. A signal pulse was generated every $\frac{3}{8}$ wavelength (0.134 inch) using a 342 kilohertz center frequency for the transducer signal. In digitizing the received signal a sampling rate of 912 kilohertz, or more than twice the highest frequency in the ultrasonic pulse, was used to satisfy the Nyquist condition for signal sampling. Thus, 90 samples were taken for each foot of the pipe, and using a sample interval corresponding to four feet, 360 wavetrains were averaged in inspecting each four feet of the tube, producing a theoretical signal to noise ratio improvement of 25.6 db for random noise.

The method and apparatus for ultrasonic inspection of a body in accordance with the present invention is particularly useful in inspection of tubes as used in steam driven electrical power generation equipment. However, the invention can be applied to inspect other structures where the transmitter and receiver can be moved during inspection.

Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. The method of ultrasonically inspecting a structure for defects with a moving inspection means and distinguishing between defects along the line of travel comprising the steps of periodically introducing an ultrasonic wave in said structure by transducer means, moving said transducer means relative to said body between ultrasonic wave introductions, receiving ultrasonic waves by said transducer means during an interval of time after each introduction of waves, adjusting the time references of said received waves to compensate for displacement of said transducer means whereby waves coming from the direction of travel are distinguished from other waves, said step including delaying said received wave by a time equal to twice the displacement of said transducer means between introduction of waves into said structure divided by the velocity of said ultrasonic wave and said displacement is a multiple of said ultrasonic wave speed times one-half the sample time interval of a received wave, said step of adjusting the time reference of said received wave further assuming that said wave is received from the direction from which said transducer means is moved and said step further including advancing said received wave by a time equal to twice the displacement of said transducer means between introduction of waves into said structure divided by the velocity of said ultrasonic wave, summing said received waves after adjusting the time references thereof, and analyzing said summed wave.

2. The method as defined by claim 1 wherein said transducer means includes a separate transmitter and a separate receiver and said step of adjusting the time reference of the received wave further assumes that waves are received directly from said transmitter to said receiver and said step further includes summing said received waves without adjustment of said received waves.

3. The method as defined by claim 1 wherein said transducer means displacement is an odd multiple of one-eighth the wavelength of said ultrasonic wave.

4. Apparatus for ultrasonic inspection of a structure for defects using a moving inspection means and distinguishing between defects along the line of travel comprising transducer means for periodically introducing an ultrasonic wave into said structure, means for moving said transducer means relative to said structure, transducer means for receiving ultrasonic waves in said structure during an interval of time after each introduction of waves, means for adjusting the time reference of each received wave to compensate for movement of said transducer means and distinguish waves in the direction in which said transducer means is moving, said received waves being delayed by a time interval equal to twice the displacement of said transducer means between introduction of waves into said body divided by the velocity of said ultrasonic waves, said displacement of said transducer means being a multiple of speed of said ultrasonic waves multiplied by one-half of the received sample time interval, said adjusting means also advancing received waves by a time interval equal to twice the displacement of said transducer means between introduction of waves divided by the velocity of said ultrasonic waves whereby waves coming from the direction from which said transducer means is moving are distinguished, and means for summing said received waves after adjusting the time references thereof.

5. Apparatus as defined by claim 4 wherein said means for summing also sums received waves without adjustment of time references to distinguish waves reflected from defects lying between said transducer means for introducing ultrasonic waves and said transducer means for receiving ultrasonic waves.

6. Apparatus as defined by claim 5 wherein said means for receiving and storing said ultrasonic waves comprises means for digitizing said received signals and said summing means includes a plurality of buffer storage means for receiving said received signals for time reference adjustment.

* * * * *